United States Patent
Petersen (10) Patent No.: US 8,034,017 B2
(45) Date of Patent: Oct. 11, 2011

(54) METHOD AND APPARATUS FOR HOME DIALYSIS

(75) Inventor: Robert Smith Petersen, Fanø (DK)

(73) Assignee: FlexDialysis ApS, Rungsted Kyst (DK)

( * ) Notice: Subject to any disclaimer, the term of this patent is extended or adjusted under 35 U.S.C. 154(b) by 443 days.

(21) Appl. No.: 12/159,065

(22) PCT Filed: Dec. 29, 2006

(86) PCT No.: PCT/DK2006/000752
§ 371 (c)(1),
(2), (4) Date: Jun. 24, 2008

(87) PCT Pub. No.: WO2007/073739
PCT Pub. Date: Jul. 5, 2007

(65) Prior Publication Data
US 2009/0036825 A1    Feb. 5, 2009

(30) Foreign Application Priority Data

Dec. 29, 2005   (DK) .................................. 2005 01848

(51) Int. Cl.
*A61M 1/00*    (2006.01)
(52) U.S. Cl. ............ 604/29; 604/132; 604/133; 604/28; 210/321.71
(58) Field of Classification Search .................. 604/132, 604/133, 29, 28; 210/321.71
See application file for complete search history.

(56) References Cited

U.S. PATENT DOCUMENTS

| | | | |
|---|---|---|---|
| 3,761,586 A * | 9/1973 | Matsumoto et al. | 424/542 |
| 6,303,036 B1 | 10/2001 | Collins et al. | 210/646 |
| 6,913,590 B2 | 7/2005 | Sorenson et al. | 604/29 |
| 2002/0023879 A1 * | 2/2002 | Hadden | 210/646 |
| 2002/0091371 A1 | 7/2002 | Ritter | 604/408 |
| 2003/0097086 A1 | 5/2003 | Gura | 604/5.01 |
| 2007/0278155 A1 | 12/2007 | Lo et al. | 210/646 |

FOREIGN PATENT DOCUMENTS

| | | |
|---|---|---|
| DE | 81 17 448 U1 | 11/1981 |
| DE | 103 57 835 A1 | 7/2005 |
| EP | 0 619 135 A1 | 10/1994 |
| FR | 2 345 165 A1 | 10/1997 |
| GB | 2 063 704 A | 6/1981 |
| GB | 2063704  * | 6/1981 |
| JP | 2002045420 A | 2/2002 |
| JP | 2003062067 A | 3/2003 |

(Continued)

OTHER PUBLICATIONS

International Search Report PCT/DK2006/000752 Dated Mar. 28, 2007.

(Continued)

*Primary Examiner* — Kevin C Sirmons
*Assistant Examiner* — Brandy C Scott
(74) *Attorney, Agent, or Firm* — Winston & Strawn LLP (57) ABSTRACT

A system, process, and method for home hemodialysis or peritoneal dialysis to be carried out by the patient or other non-professional users based upon re-circulation of dialysate from small dialysate containers which allows for very small dialysate consumption and easy portability. The system thereby also allow for long-duration dialysis without use of large volumes of dialysate. The invention may be implemented as a hemodialysis system, a process for administering dialysate, or as a method for performing dialysis.

21 Claims, 6 Drawing Sheets

FOREIGN PATENT DOCUMENTS

| | | |
|---|---|---|
| JP | 2005510304 | 4/2005 |
| WO | WO 2004/008826 A2 | 1/2004 |
| WO | WO 2005/063166 A1 | 7/2005 |
| WO | WO 2007/140241 A1 | 12/2007 |

OTHER PUBLICATIONS

European Standard Search Report, DK 2005/01848, dated Nov. 13, 2006.

Cambi, Vincenzo et al., "Critical Appraisal of Haemofiltration and Ultra-Filtration. The Development of Ultra-Short Dialysis: Preliminary Results", Journal of Dialysis, vol. 2, No. 2, pp. 143-154 (1978).

Van Stone, John C., "Dialysis Equipment and Dialysate, Past, Present and the Future", Seminars in Nephrology, vol. 17, No. 3, pp. 214-217 (1997).

* cited by examiner

METHOD AND APPARATUS FOR HOME DIALYSIS

This application is a 371 filing of International Patent Application PCT/DK2006/000752 filed Dec. 29, 2006.

FIELD OF THE INVENTION

The invention relates to dialysis, in particular to haemodialysis or peritoneal dialysis carried out in the home of the patient.

BACKGROUND OF THE INVENTION

Patients with reduced or no kidney capacity are critically dependent on regular haemodialysis or peritoneal dialysis. The dialysis may be done in a hospital dialysis unit, in a clinic away from the hospital, in a self-care centre (with some assistance from the staff), or at home. Special training is needed for self-care or home dialysis.

While some home dialysis patients follow a standard schedule of four to five hours three days a week, some use nocturnal home dialysis where they go on dialysis four to six nights a week for six to eight hours while they sleep. Home dialysis greatly improves the removal of waste products from the body and has been found to improve well-being, to allow for a more liberal diet and to reduce the need for medications. This is mainly attributed to the increased dialysis time allowed by performing the dialysis in the patients' normal surroundings.

Figure 1:
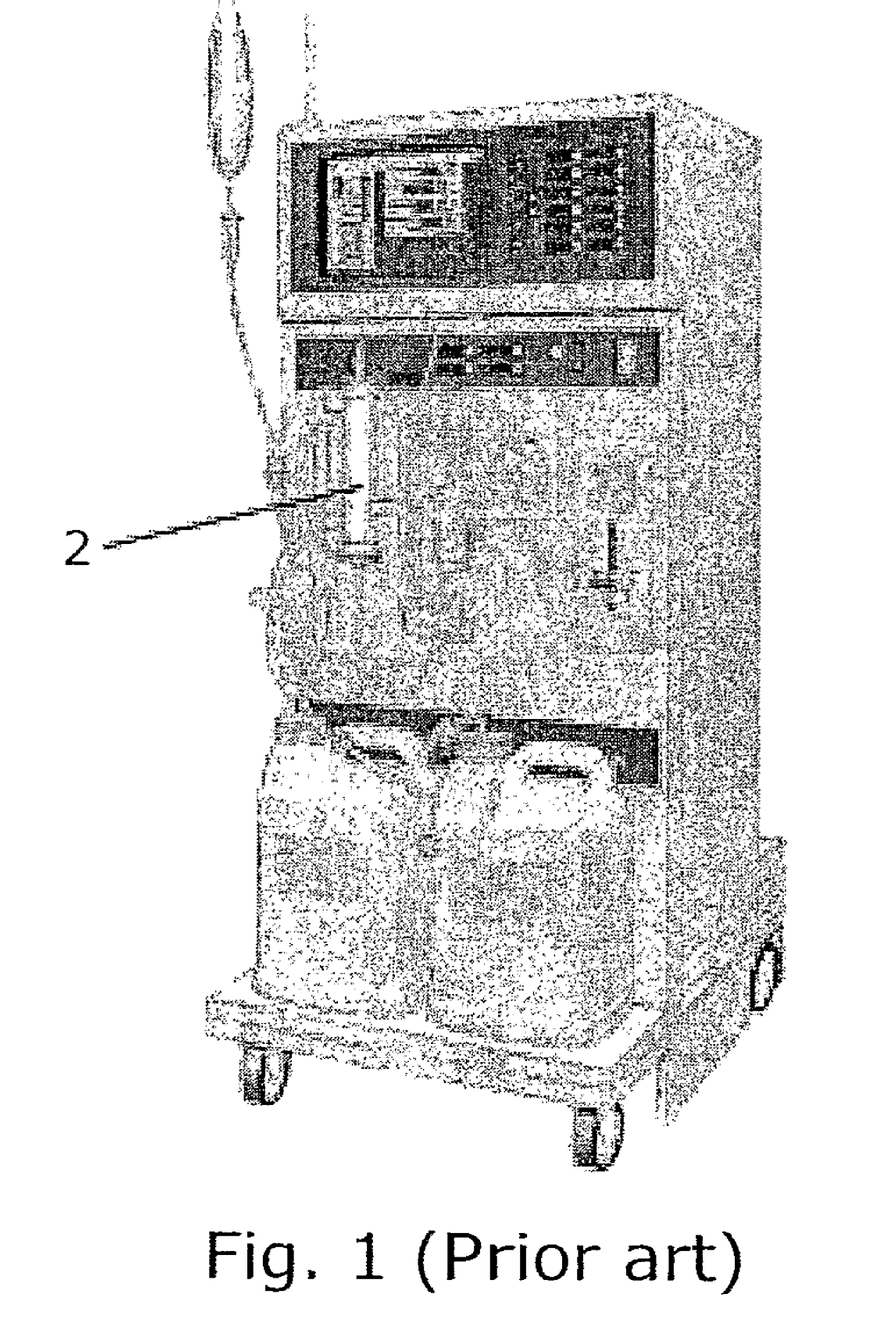
FIG. 1 is an illustration of a typical haemodialyser according to the prior art.

Present home haemodialysers (see 2 in FIG. 1) and peritoneal dialysers have several disadvantages. Their designs are based on dialysers for clinical use, which are optimised for speed (typical dialysis duration of 2-4 hours), meaning large artificial kidneys, high blood flow rate, and similarly high dialysate flow rate. The operation and user interface is typically designed for professional clinical personnel, and is too complex for the uneducated home user. In addition, they are dependent on the large-scale water purification plants generally available in clinics.

This means that present home dialysers suffer from the following drawbacks:
1. They are too complex to operate.
2. They are too large to be installed in only very spacious surroundings, and not in small private apartments.
3. They are too heavy to be moved around in the home by enfeebled persons (as many patients are or become), which is relevant if both day-time and nocturnal dialysis is to be available. The weight and size of present dialysers does not allow routinely transportation out of the home, e.g. on vacation.
4. They are not adapted to be used in dialysis with long duration, e.g. 6-8 hours.
5. They are dependent on large flow rates of dialysate and thereby on too large volumes of purified water for the dialysate preparation. Purified water can be provided by micro-purification plants installed in the home or integrated in the haemodialyser, presenting yet another operation issue to the patient. Alternatively, the prefabricated dialysate or purified water can be supplied to the home in containers, which again poses a handling problem for enfeebled persons due to the large volumes.

SUMMARY OF THE INVENTION

It is an object of the invention to provide a dialyser adapted to be used in a patient's home and to be operated by the patient, with a low dialysate consumption and adapted to perform long-duration dialysis.

A first embodiment of the invention is a haemodialysis system particularly adapted for home haemodialysis. The system comprises a haemodialyser and two or more dialysate containers connected to administer dialysate to the haemodialyser and is characterised in that:
 the dialysate containers are filled with dialysate;
 the system further comprises at least one empty or partially filled flexible dialysate container;
 the dialysate containers hold a volume not exceeding 10 L;
 the dialysate containers are connected between the outlet and inlet of the haemodialyser so that dialysate leaving the haemodialyser from the outlet will be recirculated to the inlet of the haemodialyser.

In one form of dialysis, peritoneal dialysis, a dialysate solution is run through a tube into the peritoneal cavity where it absorbs waste products. The fluid can be left in the peritoneal cavity for a prescribed amount of time and then be replaced or it can be continually replaced by proving a flow (requires two catheters or a dual-lumen catheter). Another form, haemodialysis, involves diffusion of solutes across a semipermeable membrane in an extracorporeal circuit where the dialysate is flowing in the opposite direction to blood flow on opposite sides of the membrane. The present invention may be applied in both peritoneal dialysis and haemodialysis, commonly referred to herein as dialysis. Similarly, apparatus' for carrying out these forms of dialysis are referred to as dialysers. Examples and embodiments are mainly given in relation to haemodialysis.

Preferably, the dialyser comprises pumping means and a dialysate flow pathway configured to facilitate the re-circulation dialysate from a dialysate outlet of the dialyser to a dialysate inlet of the dialyser through the dialysate containers there between.

Traditionally, measure of dialysis efficiency has been based on elimination of molecules such as urea and creatinine from the blood. These molecules are small, with typical molecular weights of about 60 au. It has been realised that other, heavier substances also have a large impact on the poisoning suffered by kidney cases, which have molecular weights in the range of 1.000-2.000 au, and even as high as 10.000 au. Such large molecules move around in the organism more slowly than small molecules—their diffusion from tissue to the blood takes place at a much slower rate.

The slow diffusion of the significant substances means that short-duration haemodialysis has a diminished effect on their elimination. Therefore, using haemodialysis with smaller blood and dialysate flow rates, but performed over longer time, is advantageous. Also, since the elimination of the significant substances occurs at slow rates, their concentration in the used dialysate is relatively small.

It is therefore an essential element of the present invention that the dialysate is recirculated, meaning that dialysate that have already passed the artificial kidney is collected and lead to the inlet of the haemodialyser for another pass. Similar considerations applies to peritoneal dialysis. Recirculation of dialysate provides the advantage of a significantly reduced consumption of total dialysate volume as the same volume is used several times. The reduced consumption and thereby smaller required volume of dialysate provides a number of additional advantages:

Since smaller dialysate volumes are required, the costs and work involved in obtaining dialysate is reduced. Supplying centrally prepared dialysate fabricated at a professional dialysate preparation plant or site to the home is made easier, and so is the work involved for patients' or relatives own preparation of dialysate from tap-water.

The smaller dialysate volumes also allow for using better quality dialysate for a competitive price. Since the quality of the dialysate is among other parameters determined by the purity of the applied water and since very pure water is not readily available, it is an advantage that the reduced dialysate consumption allows use of smaller amounts of such water.

Smaller volumes of dialysate means less dialysate to be handled by the patient. By handling dialysate in relatively small and easy to handle containers, even weak patients can set up a dialysis procedure without assistance. Long-duration haemodialysis using prior art haemodialysers often requires handling of as much as 70-120 L of dialysate—an immense volume to handle on a daily basis for most patients. The system according to the present invention comprises containers which can be handled by patients, preferably containers holding a volume not exceeding 10 L of dialysate, such as not exceeding 8 L of dialysate. For weaker patients, it may be preferred to use containers holding a volume not exceeding 6 L of dialysate, such as not exceeding 5 L of dialysate in the system.

The feature that dialysate is re-circulated so that only manageable amounts are needed means that the dialysate circulates in a closed system. This has the advantage that no admission to drainage for used dialysate is required, making the system more transportable and flexible.

An important advantage of the low dialysate consumption is that it allows for even very long-duration dialysis using relatively cheap and manageable volumes of dialysate. As touched upon previously, the duration dialysis has been shown to be one of the most important factors in patient well-being, with long duration dialysis being better. In hospitals and clinics, efficiency and speed must be weighed when assessing dialysis duration, whereas for home dialysis where the patients daily routines can be adapted to the dialysis. Long-term dialysis may be particularly relevant for bedfast patients.

As the dialysate re-circulates, the total volume increases as fluid is drawn from the patient through the artificial kidney of the haemodialyser. To accommodate this fluid retention, the empty or only partially filled container is preferably capable of receiving at least 1 L fluid accumulated by the haemodialyser.

In one embodiment, the dialysate containers are filled with centrally prepared dialysate. This dialysate is preferably ready-to-use without any pre-treatment required by the patient. Applying centrally prepared dialysate provides the advantage of using high-end large-scale production plants leading to reduced fabrication costs and increased quality. It is a further advantage that it eliminates the need for the patient to house and operate water purification systems and that it increases transportability of the system. Hence, centrally prepared dialysate preferably contains physiological levels of electrolytes. Applicable electrolyte levels cover a range of concentrations which may be adjusted to special circumstances but which are also a matter of personal preference and opinion of the responsible doctor. Typical values for common electrolytes are:

| | |
|---|---|
| Na | 130-145 mmol/l |
| K | 0-3 mmol/l |
| Ca | 1.0-1.75 mmol/l |
| Mg | 0.2-0.6 mmol/l |
| Cl | 90-110 mmol/l |

The centrally prepared dialysate preferably comprises water with an endotoxin concentration lower than 0.05 iu/ml. Preferably, the water is ultrapure water or biopure water which is sterile, pyrogen free, has a total solids content of less than 1 ppm and a maximum at 0.1 CFU (colony forming units).

The pH of the centrally prepared dialysate preferably has a physiological level, such as within [5.50-7.45]. pH buffer systems based on bicarbonate, acetate or lactate are commonly used, and may be used to ensure a proper pH in the centrally prepared dialysate. Solutions based on bicarbonate are presently not completely temporally stable, but are typically provided in two-chamber bags with a guaranteed pH of at least 24 hours after breaking the membrane. Systems based on acetate or lactate are temporally stable, but are used less often since some patients have difficulties in metabolizing large amounts of acetate. This last problem is lessened with the present invention. Since the total amount of dialysate is significantly reduced, so is the total quantity of buffer. During recirculation, the buffer concentration, and thereby the absorption rate, slowly decreases as an equilibrium is approached. As a result, the quantity of buffer absorbed by the patient is considerably smaller with the system of the present invention.

In another embodiment, the dialysate containers are filled with dialysate prepared from tap water, typically in the home of the patient. In this embodiment, the dialysis system may comprise a filter for filtering the tap water to increase the purity. Further, the system may comprise connectors, adapters for filling the dialysate containers with purified tap water. The system may further comprise means for administering pre-mixed compositions of buffers and electrolytes (as salts or solutions) to the purified tap water to obtain a dialysate with properties similar to the centrally prepared dialysate described in the above.

When referring to prefabricated or supplied dialysate in the remainder of the application, this means that the dialysate is supplied at least partly prefabricated to the dialyser in the dialysate containers, and it is understood that this dialysate is may be centrally prepared or prepared in the home of the user based on filtering and treatment of tap water.

Some dialysers can adjust electrolyte concentration and pH of the supplied dialysate, meaning extra complications in operation and maintenance as well as increased price. Hence, according to a preferred embodiment, the system according to the invention does not add substances or comprise options for regulating electrolyte levels or pH to the dialysate from the dialysate containers, and it applies the prefabricated dialysate directly from the containers without prior modification. However, to allow for long-term storage of filled dialysate containers, the system may apply containers having two or more chambers separated by a membrane which when broken prior to use mixes solutions resulting in a dialysate with physiological electrolyte levels an pH.

The number of times a given volume of dialysate is recycled when using the present system is determined by operation parameters comprising: the flow rate, F, of dialysate trough the haemodialyser; the duration, $t_D$, of the haemodialysis; the total volume, $V_{total}$, of prefabricated dialysate in the containers; and the amount of liquid accumulated from the patient during dialysis. As the accumulated volume typically constitutes less than 5% of the total volume, it is disregarded in the following for the purpose of simplicity. To quantify the recirculation, a recirculation degree, RD, is defined as the number of times any volume of dialysate passes the artificial kidney of the haemodialyser during a dialysis; $RD = F \times t_D / V_{total}$.

Recycling the dialysate only one or two times means that only small quantities of the large molecules will have diffused to the dialysate, meaning a low degree of utilization for the dialysate (and larger required volume for a given flow rate and duration). Recycling the dialysate too many times yield high concentrations of the large molecules and other extracted substances, leading to a very poor and inefficient performance during the last cycles. It is preferred that the dialyser applied in the invention further comprises means for calculating and adjusting a first operation parameter (such as the dialysate flow rate) based on given values of the other operation parameters (such as desired dialysis duration and total dialysate volume in the connected dialysate containers) to provide a recirculation degree in the interval [3.5; 6]. Either of the flow rate, duration or total volume may be input to the dialyser by the patient or operator.

The dialyser and the dialysate containers according to the invention are preferably designed to be used by persons with little or no training. Therefore, it is preferred that all connections, such as inlet/outlet of the dialyser and input/output of containers and end parts of any tubes or pipes used in connecting these, are designed either to have physical constraints which only allows correct assembly and connection and/or to be connectable in several ways which are all correct. Also, it is preferred that the dialyser requires as little input from the patient or operator as possible in order to initiate dialysis. Hence, in a preferred embodiment, the total dialysate volume is automatically detected when the patient has connected the containers. Here, the system may comprise a scale for weighing the connected dialysate containers and estimating a total dialysate volume, and means for supplying the estimated volume to the means for calculating the flow rate. The amount of accumulated fluid which is to be eliminated during the dialysis is preferably also specified by the patient. This may be done by typing in a desired volume to be eliminated, e.g. 0.75 L or by indicating the present weight of the patient, which the dialyser can compare with a predefined optimum weight. Thereby, only the desired dialysis duration and fluid elimination need to be specified by the operator to initiate dialysis.

To improve transportability, it may be preferred that the dialyser is designed to have a dry weight of less than 15 Kg, preferably less than 10 Kg. Optionally, the dialyser may be formed by two or more easily separable parts, such as one part having scale and electronic processing unit and one part having pumps, tubing and connectors for both the blood and dialysate circuits and the artificial kidney.

Preferably, the invention applies disposable dialysate containers having a volume not exceeding 10 L and having sealed dialysate input and output adapted to provide liquid connections to other dialysate containers and inlet/outlet of a dialyser. The dialysate containers may be subject to the features relating to dialysate containers and the dialysate described in relation to the first embodiment.

In addition, it may be advantageous too that the dialysate containers comprise access for administering or extracting fluids or additives to/from the dialysate containers, continuously, such as by a drip, or according to requirement. Dialysate samples may be extracted by the patient and sent to analysis at a central laboratory to determine the elimination of toxic substances e.g. urea, sodium and phosphate. Further, an access opens possibility of continuous analysing the elimination rate of waste products. Alternatively, the access may be applied to administer a drug or nutritious substances (e.g. glucose, vitamins or minerals) to the dialysate and thereby to the patient.

A second embodiment of the invention is a process of administering dialysate to a dialyser, the process comprising:
  providing a dialyser having a dialysate inlet and outlet and pumping means for circulating dialysate in the dialyser and the containers;
  providing flexible dialysate containers having input and output openings for providing liquid connections;
  connecting the dialysate containers to the inlet of the dialyser;
the process being characterised in that:
  the step of providing the dialysate containers comprises providing dialysate containers holding dialysate and at least one empty or partially filled flexible dialysate container;
  the dialysate containers each have a volume not exceeding 10 L;
  the step of connecting the dialysate containers to the dialyser comprises the step of connecting the dialysate containers between the inlet and outlet of the dialyser;
  the method further comprises the step of re-circulating the dialysate from the outlet of the dialyser to the inlet of the dialyser through the connected dialysate containers by activation of the pumping means.

The process of administering dialysate to a dialyser is a technical procedure and not a treatment. The step of providing dialysate containers holding dialysate may be implemented by providing containers holding centrally prepared dialysate or by an operator filling the containers with purified tap water with additives, and connecting the provided filled containers to the dialyser.

A third embodiment of the invention is a method for performing dialysis comprising:
  providing a dialyser having a dialysate inlet and outlet and pumping means for circulating dialysate in the dialyser and the containers;
  providing two or more flexible dialysate containers holding dialysate, each having a volume not exceeding 10 L and an input and an output for providing liquid connections to other dialysate containers and the inlet/outlet of the dialyser;
  providing at least one empty or partially filled flexible dialysate container;
  connecting the provided dialysate containers in series and/or in parallel between the inlet and outlet of the dialyser;
  connecting the dialyser to a subject and performing dialysis; and
  circulating the dialysate from the outlet of the dialyser to the inlet of the dialyser through the connected dialysate containers.

Preferably, the method further comprises the step of adjusting the dialysate flow rate of the dialyser based on a desired dialysis duration a total dialysate volume in the connected containers to provide a recirculation degree in the interval [3.5; 6]. Also, it is preferred that desired dialysis duration is the only parameter to be directly specified to the dialyser by the operator, such as by typing on a keyboard or equivalent.

Recirculation of dialysate is mentioned in the prior art, see e.g. *Dialysis equipment and dialysate, past, present and the future* by John C van Stone in Seminars in Nephrology, Vol 11, No 3, 1999 p. 214-217; and *Critical appraisal of haemo-*

*filtration and ultra-filtration, the development of ultra-short dialysis* by Cambi et al. in Journal of Dialysis, Vol 2, 1978 p. 143-154.

The van Stone article is a historical review, It describes how tanks most often made of glass or steel, containing 100 liters of tap water, were mixed with dry chemicals and used a batch of dialysate. As these tanks were awkward to handle, this technique has been abandoned. However, van Stone speculates on future developments (1997) and he imagines that in the future a dialysis machine will be developed, which can be used at home on a daily basis, and that the amount of dialysis a patient receives will be measured and recorded during every dialysis treatment. The Cambi article describes a system for use in research. The authors used a system described as "a batch type delivery system filled with 20 or 40 liters of normal dialysis solution"—a one-chamber-tank-system. The patients were treated for only 2 hours 3 times a week. The system was unable to keep the patients pH-values within acceptable limits, so the patients required continuous intravenous infusion of sodium bicarbonate during the dialysis sessions. The infusion-rate was 50-80 milimoles per hour. Because of the very short treatment time per session, the authors themselves foresee that the system is inadequate with respect to removing medium sized molecules (and larger molecules). Data are given after "a few weeks of treatment", the trial was cancelled after 4 months. None of these references describe a system which can be used for home haemodialysis.

One important problem solved by the invention is how to make home dialysis easier for kidney patients. The idea underlying the invention relates to a system based on recirculation of dialysate, which allows for very small dialysate consumption which in turn, as specified previously, allows for a number of advantageous features not realised in the prior art. These features provides a system for home dialysis which is easy to use, has improved portability, provides high quality dialysate, and allows for long duration dialysis.

DETAILED DESCRIPTION OF THE INVENTION

Figure 2:
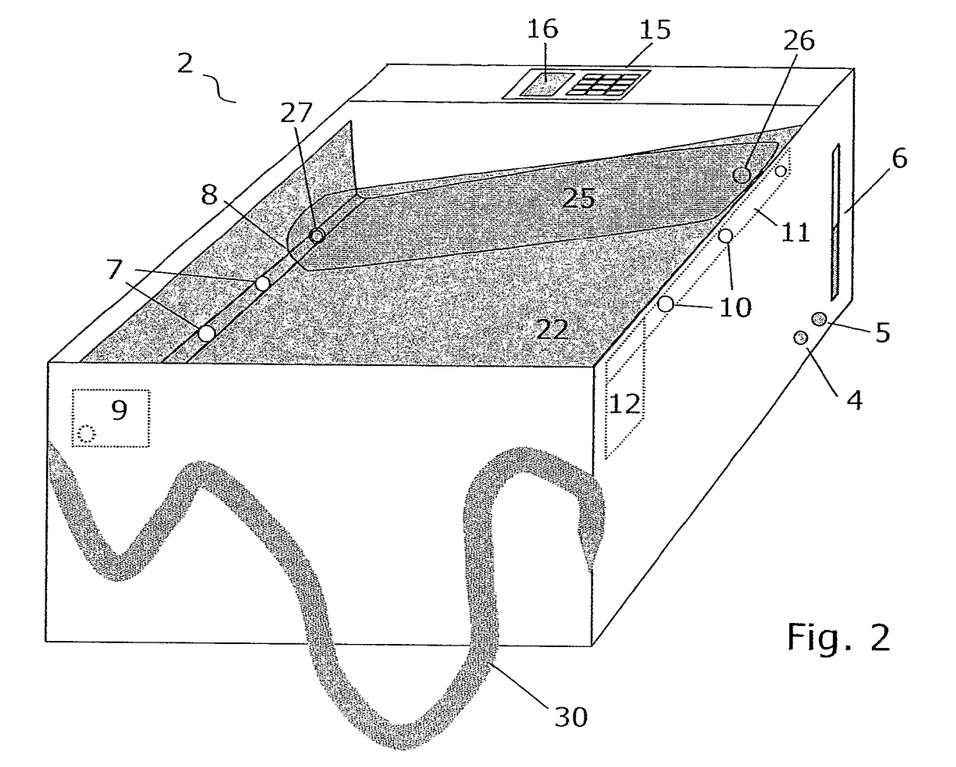
FIG. 2 is a perspective illustration of a dialyser for use in the present invention.

FIG. 2 illustrates a possible layout of a dialyser 2 for use in a system according to an embodiment of the invention. Punctured lines indicates features inside the dialyser. Some features typically included in dialysers but which are not relevant in relation to the present invention, have been omitted. Although the looks and exterior design of the illustrated dialysers are different from known dialysers, most technical components (pumps, artificial kidneys, sensors, valves, etc.) are similar and perform similar functions. The main difference being that the flow pathway of the dialysate is designed to re-circulate the dialysate after it has passed through the artificial kidney, which requires some changes in the pipes and pumping. These changes, however, are considered within the abilities of the person skilled in constructing dialysers when being presented with the present description.

The dialyser 2 is a haemodialyser having blood inlet 4 and outlet 5 to be connected to the blood system of the patient, as well as a blood pump (not shown) and a blood flow indicator 6. Commercially available tubes, needles and artificial kidneys may be used for this purpose. The blood is circulated through one side of the artificial kidney of the haemodialyser (not shown), while dialysate is circulated through the other side of the artificial kidney. For this purpose, the dialyser has a dialysate circulating system comprising one or more inlets 7 for receiving dialysate and one or more outlets 10 for leading used dialysate out from the dialyser. Inlets and outlets are in fluid connection with inlet/outlet pipes 8 and 11, respectively, for leading the dialysate to and from the artificial kidney. One pump 9 connected to inlet pipe 9 regulates the inflow of dialysate from connected containers to the artificial kidney, while another pump 12 connected to outlet pipe 11 regulates the flow from the artificial kidney and back to the connected containers 25 for recirculation. The inlets 7, outlets 10, pipes 8 and 11, pumps 9 and 12, and connected dialysate containers are commonly referred to as the dialysate flow system.

The haemodialyser 2 has a keyboard 15 for the patient to enter e.g. the desired dialysis duration and fluid retention elimination, and display 16 for providing feedback, status, and confirmation to the patient. To aid the transportability, the dialyser may have a carrying strap 30 or a handle (not shown).

The dialyser 2 is adapted to hold the provided dialysate containers 25, e.g. so that the dialysate containers 25 rest on surface 22. Surface 22 is also connected to a scale for weighing the dialysate containers and their content. Thereby, the haemodialyser 2 can automatically estimate the volume of dialysate in the connected containers, both before and after the dialysis.

The dialysate containers 25 are preferably flexible and have an input 26 and an output 27. To ensure dialysate flow through the containers, they are oriented with input 26 connected to outlet 10 of the haemodialyser and output 27 connected to inlet 7. By making the surface 22 slightly inclining, it is ensured that dialysate in the dialysate container will always collect itself over the output 27.

Figure 3:
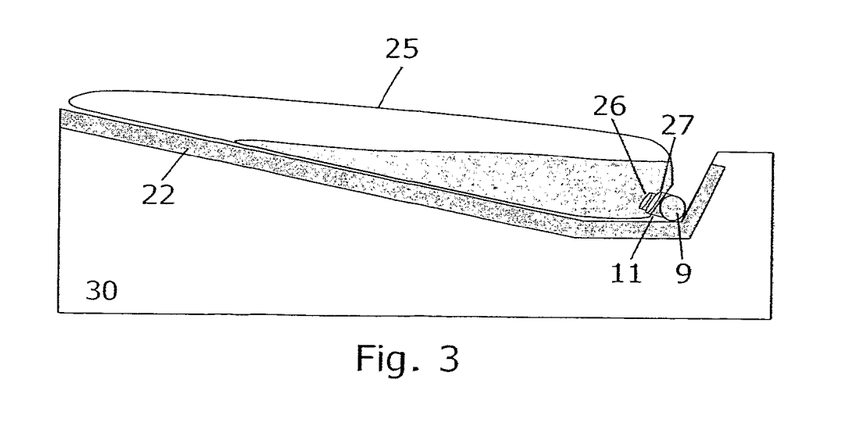
FIG. 3 is a cross-sectional illustration of a dialyser for use in the present invention.

FIG. 3 is a cross-sectional illustration of a haemodialyser 30 similar to the haemodialyser 2 of FIG. 2, but with a different layout of the dialysate flow system. Here, input 26 and output 27 of the dialysate container 25 are formed in the same, lower end, where the input pipe 9 and output pipe 11 are also formed.

In a peritoneal dialyser, the dialysate is traditionally left in the peritoneal cavity to be completely and automatically replaced several times by the dialyser. Newer peritoneal dialysers allows for a flow of dialysate by using two lumens into the peritoneal cavity. In the last type, the dialysate can be recirculated with the same advantages as for the haemodialyser. Here, instead of recirculating dialysate to the artificial kidney, dialysate is recirculated trough the two lumens to the peritoneal cavity.

Figure 4:
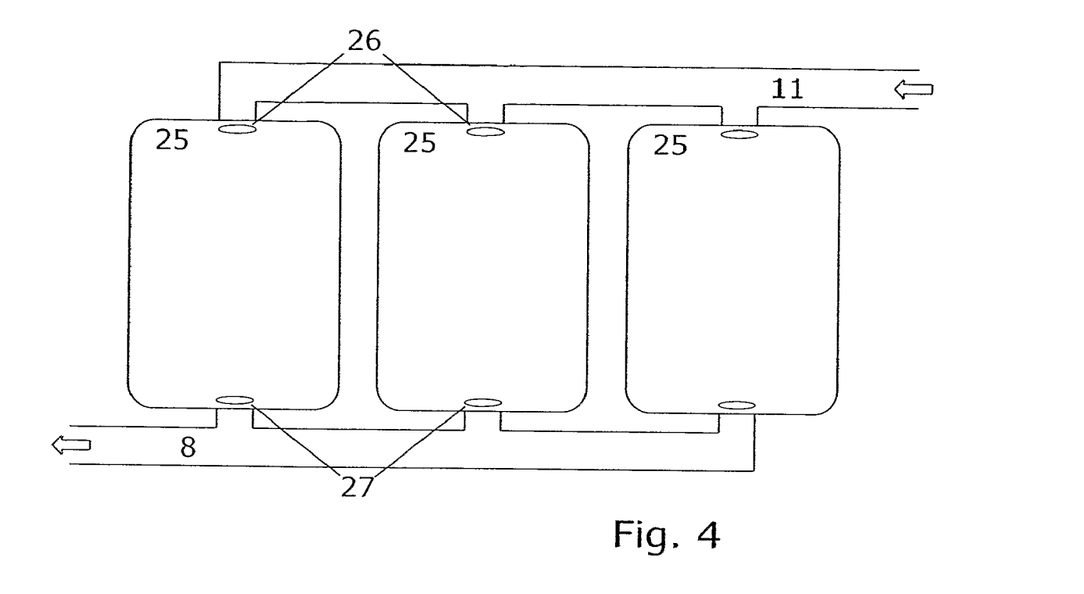
FIGS. 4-7 illustrate various layouts of the dialysate flow system.
Figure 5:
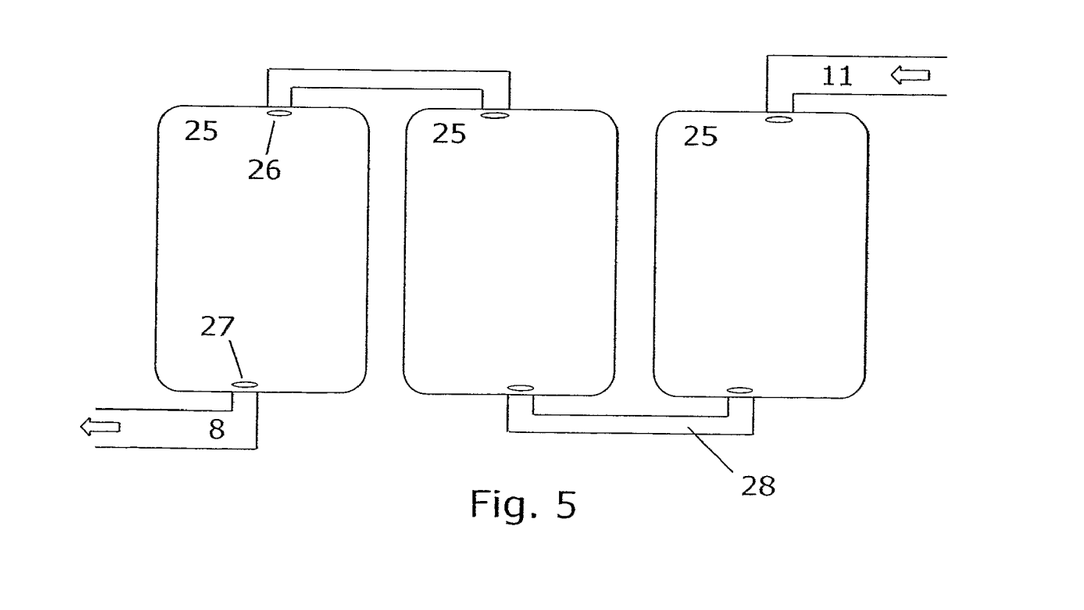

FIGS. 4-7 show different layouts of the dialysate flow system. In FIG. 4, the dialysate containers 25 are connected in parallel with inputs 26 and outputs 27 positioned in opposite ends, which ensures proper mixing of dialysate. In FIG. 5, the dialysate containers 25 are connected in series with intermediate tubing 28 interconnecting containers.

Figure 6:
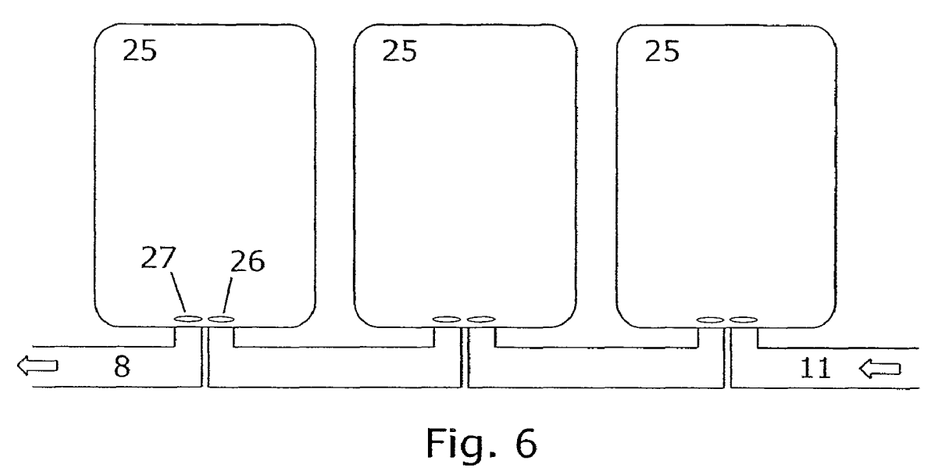
Figure 7:
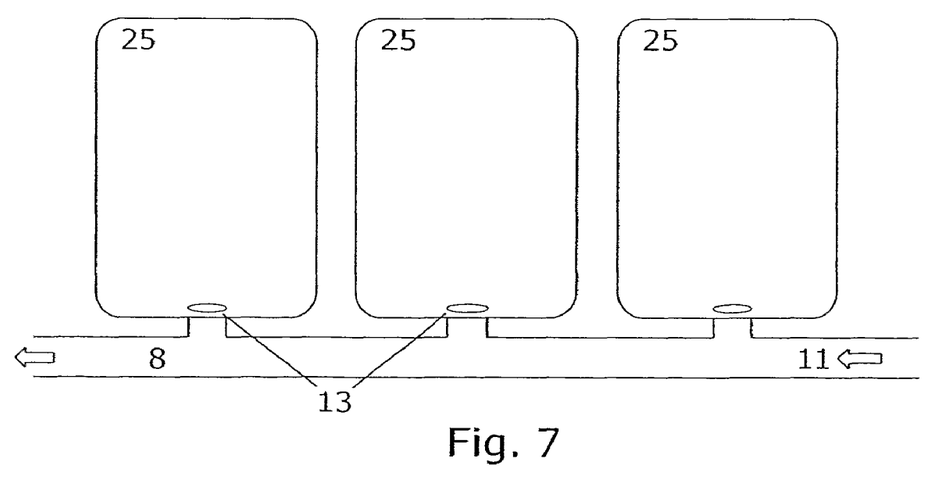

FIG. 6 shows another possible dialysate flow system layout with dialysate containers 25 connected in series. Here, the input 26 and output 27 of each dialysate container 25 are positioned in the same end part of the dialysate container, which makes the flow path of the dialysate flow system simpler. In FIG. 7, the input and output of each dialysate container are provided by one opening, which has the advantage of making the process of interconnecting dialysate containers simpler.

In all layouts, it is important that there is room for holding the liquid extracted from the patient. This can be done by providing an empty or partially filled container in the flow system.

The dialysate containers may be fabricated in materials such as PVC, which makes them cheap and disposable and renders autoclaving and other cleaning unnecessary.

Figure 8:
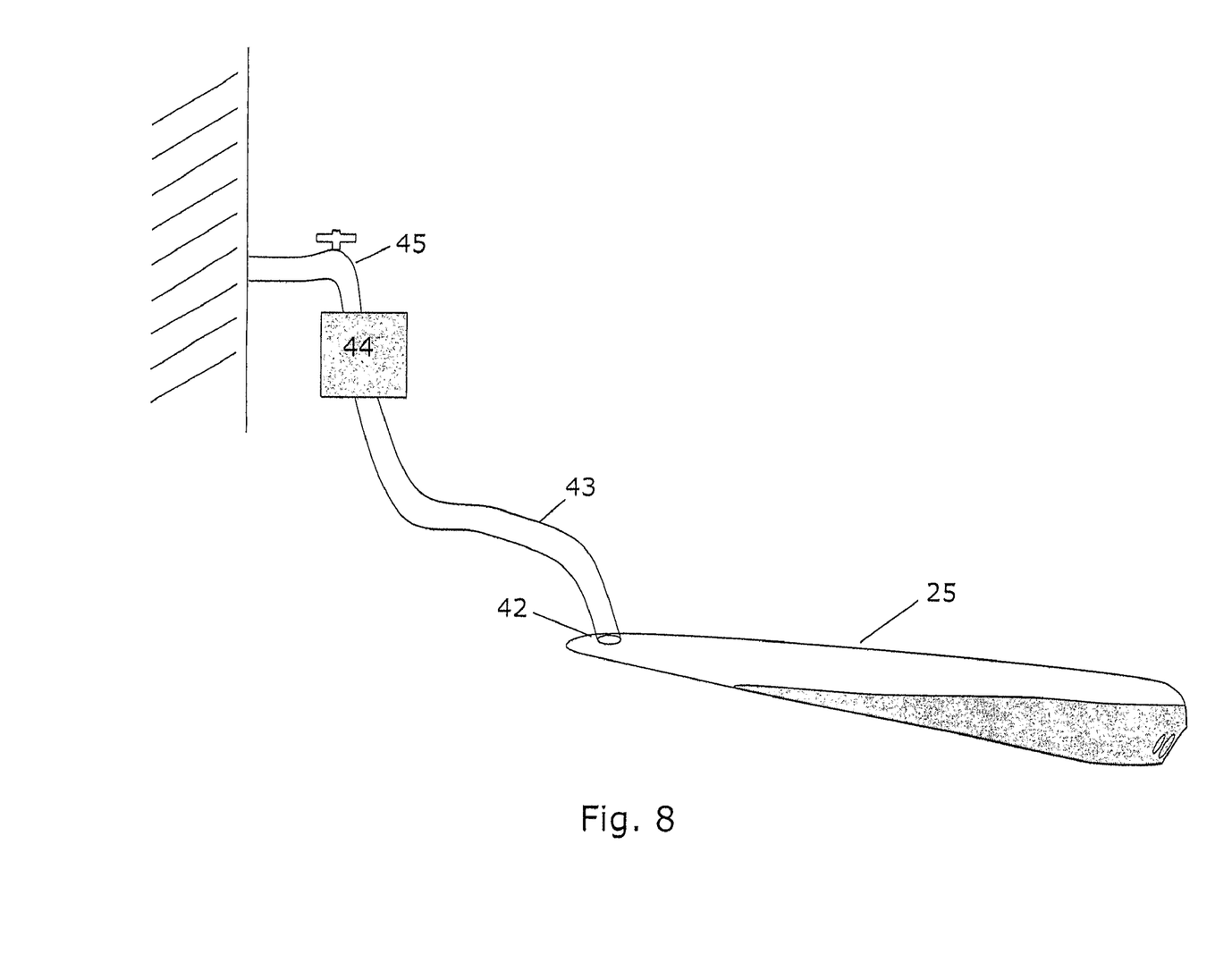
FIG. 8 illustrates a system for filling the dialysate containers with purified tap water.

As described previously, the dialysate containers may be filled by centrally prepared dialysate or by dialysate prepared from tap water at the home of the patient. FIG. 8 illustrates a setup with a dialysate container 25 being filled with water from tap 45 through filter 44 and connector 43. Adapters (not shown) for connecting the filter to the tap may be included. The setup may also comprise means for supplying additives (e.g. buffers and electrolytes) to the filtered water, e.g. by adding additives through opening 42 prior to filling of the container through connector 43. Filters or purifiers suitable for preparation of dialysate from tap water has been described in e.g. U.S. Pat. No. 6,719,745, which describes a filtering device for producing a quality of water suitable for injection into the human body.

Figure 9:
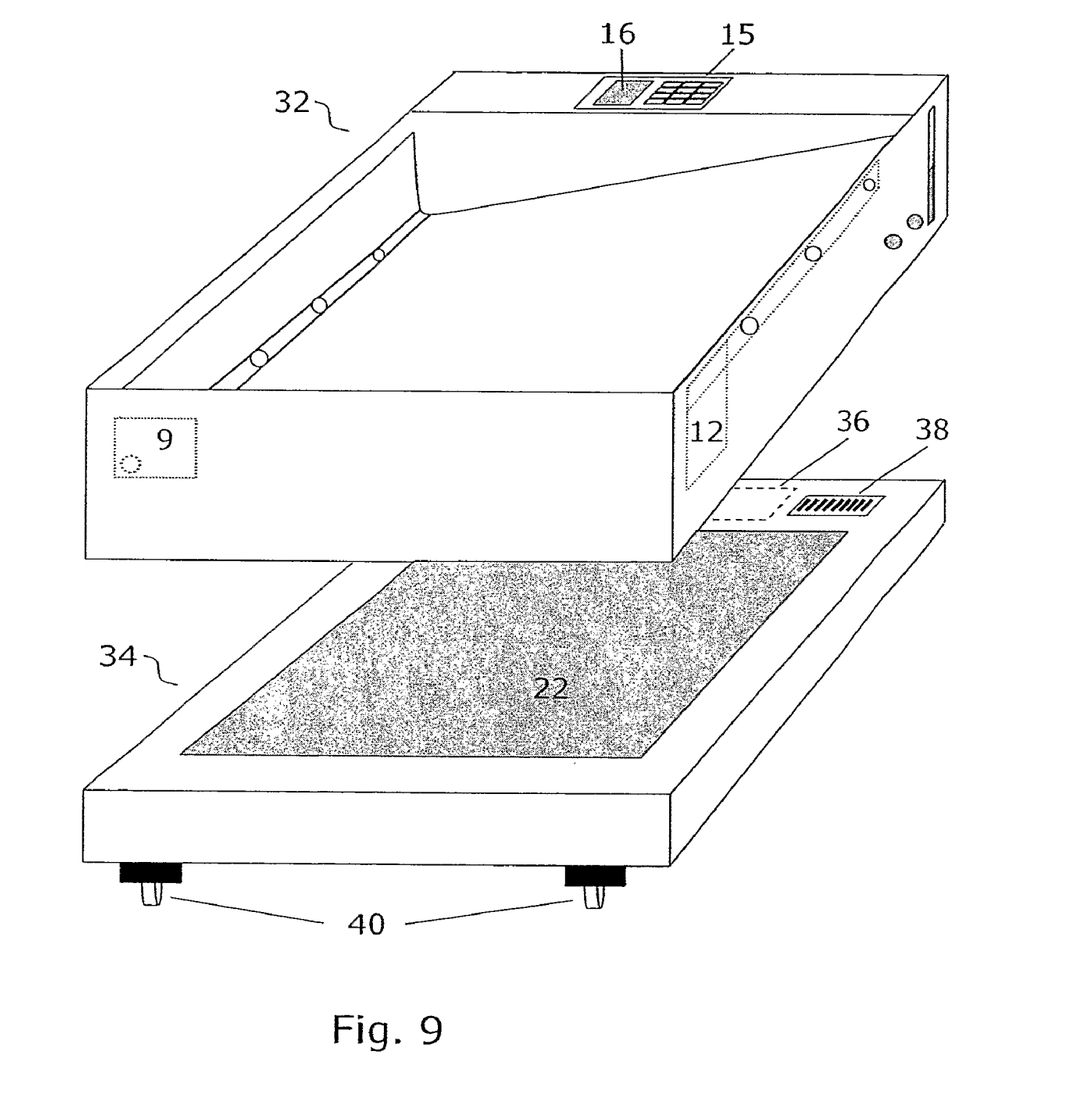
FIG. 9 is an illustration of a dialyser according to an embodiment of the invention.

In another embodiment, the dialyser is fabricated in two parts which can be separated and transported separately. Each part will be considerably lighter than the total apparatus, and which provides improved handling and increased transportability. An example of such dialyser is illustrated in FIG. 9. In the example, the dialyser has two parts 32 and 34, with lower part 32 comprising scale 22, electronic processing unit 36 and interface port 38 with a counterpart (not shown) in the upper part 32. The upper part 32 holds pumps (9, 12 and a blood pump), tubing and connectors for both the dialysate and blood circuits, as well as conveniently placed keypad 15 and display 16. The electronic processing unit 36 may be held in the upper part as well. Carrying handles may be provided on both parts and a set of wheels 40 may ease transport of the assembled dialyser.

Since the scale is held by the lower part 34, the entire upper part may be weighed. This is advantageous, since it does not matter whether the dialysate is in the containers or in the tubing of the dialyser. When the weight of the empty upper part 32 is programmed into the dialyser, the total amount of dialysate can be determined. Also a more precise difference between start weight and end weight can be calculated to determine the amount of eliminated liquid, since residual dialysate in tubing is included in the weighing.

The invention claimed is:

1. A home dialysis system comprising:
a dialyser; and
two or more dialysate containers connected to administer dialysate to the dialyser, with at least one of the dialysate containers being empty or partially filled; the dialysate containers holding a volume not exceeding 10 L; and the dialysate containers are connected between the outlet and inlet of the dialyser so that dialysate leaving the dialyser from the outlet will be re-circulated to the inlet of the dialyser,
wherein the connected dialysate containers are connected either in series and/or in parallel and the dialysate circulates in a closed system defined by the dialyser and the two or more connected dialysate containers.

2. The system according to claim 1, wherein the empty or only partially filled container is capable of receiving at least 1 L fluid accumulated by the dialyser.

3. The system according to claim 1, wherein the dialysate containers are flexible and positioned on an inclining substantially planar surface.

4. The system according to claim 1, wherein each dialysis container has an input, output and end part with the input and output positioned in the end part of the container.

5. The system according to claim 1, wherein each dialysis container has an input and output provided by one opening in the container.

6. The system according to claim 1, wherein each dialysis container has an input and output positioned respectively in opposite ends of the container to ensure mixing of recirculating dialysate.

7. A home dialysis comprising:
a dialyser; and
two or more dialysate containers connected to administer dialysate to the dialyser, with at least one of the dialysate containers being empty or partially filled; the dialysate containers holding a volume not exceeding 10 L; and the dialysate containers are connected between the outlet and inlet of the dialyser so that dialysate leaving the dialyser from the outlet will be re-circulated to the inlet of the dialyser,
wherein the dialyser further comprises means for calculating and adjusting a dialysate flow rate, F, of the dialyser based on a desired dialysis duration, $t_D$, and a total dialysate volume, Vtotal, in the connected dialysate containers, the flow rate being calculated to provide a recirculation degree, $RD = F \times t_D / Vtotal$, in the interval of 3.5 to 6.

8. The system according to claim 7, wherein the system further comprises a scale for weighing the connected dialysate containers and estimating a total dialysate volume, and means for supplying the estimated volume to the means for calculating and adjusting the flow rate.

9. The system according to claim 1, wherein the dialyser does not add substances for regulating electrolyte concentration or pH to the dialysate from the dialysate containers and has a dry weight of less than 15 Kg.

10. The system according to claim 1, wherein the dialyser comprises pumping means and a dialysate flow pathway configured to facilitate the re-circulation of dialysate from a dialysate outlet of the dialyser to a dialysate inlet of the dialyser through the dialysate containers located in fluid communication therebetween.

11. The system according to claim 1, wherein the dialysate containers are filled with centrally prepared dialysate and further comprising a filter for preparing tap water for use in dialysate.

12. The system according to claim 11, further comprising connectors for filling the dialysate containers with filtered tap water.

13. The system according to claim 11, wherein the dialysate contains physiological levels of electrolytes.

14. The system according to claim 11, wherein the dialysate comprises ultrapure water.

15. The system according to claim 11, wherein the dialysate comprises an acetate, lactate, bicarbonate buffer providing a pH in the range of 5.50 to 7.50.

16. A process of administering dialysate to a dialyser, which comprises:
- providing a home dialysis unit according to claim 1, wherein the dialyser has a dialysate inlet and outlet and pumping means for circulating dialysate in the dialyser and the containers;
- connecting the dialysate containers between the inlet and outlet of the dialyser; and
- re-circulating the dialysate from the outlet of the dialyser to the inlet of the dialyser through the connected dialysate containers by activation of the pumping means.

17. The process according to claim 16, wherein the providing of dialysate containers holding dialysate comprises connecting dialysate containers holding centrally prepared dialysate to the dialyser.

18. The process according to claim 17, wherein the providing of dialysate containers holding dialysate comprises filling dialysate containers with dialysate prepared from purified tap water and connecting these to the dialyser.

19. A method for performing dialysis which comprises:
- providing a home dialysis unit according to claim 1, wherein the dialyser has a dialysate inlet and outlet and pumping means for circulating dialysate in the dialyser and the containers, and wherein two or more flexible dialysate containers are provided for holding dialysate, with each having a volume not exceeding 10 L and an input and an output for providing liquid connections to other dialysate containers and the inlet/outlet of the dialyser;
- connecting the provided dialysate containers in series and/or in parallel between the inlet and outlet of the dialyser;
- connecting the dialyser to a subject and performing dialysis; and
- circulating the dialysate from the outlet of the dialyser to the inlet of the dialyser through the connected dialysate containers.

20. A method for performing dialysis which comprises:
- providing a home dialysis unit comprising a dialyser and two or more dialysate containers connected to administer dialysate to the dialyser, with at least one of the dialysate containers being empty or partially filled, the dialysate containers holding a volume not exceeding 10 L, and the dialysate containers are connected in series and/or in parallel between the outlet and inlet of the dialyser so that dialysate leaving the dialyser from the outlet will be re-circulated to the inlet of the dialyser;
- connecting the dialyser to a subject;
- performing dialysis by adjusting a dialysate flow rate, F, of the dialyser based on a desired dialysis duration, tD, and a total dialysate volume, Vtotal, in the connected dialysate containers, the flow rate being adjusted to provide a recirculation degree, $RD=F \times tD/Vtotal$, in the interval of 3.5 to 6; and
- circulating the dialysate from the outlet of the dialyser to the inlet of the dialyser through the connected dialysate containers.

21. The method according to claim 19, wherein desired dialysis duration and fluid elimination are the only parameters to be directly specified to the dialyser by the operator.

* * * * *